United States Patent
Cole et al.

(10) Patent No.: US 7,397,428 B2
(45) Date of Patent: Jul. 8, 2008

(54) COHERENT THZ EMITTER WITH DC POWER REDUCING RESISTOR

(75) Inventors: Bryan E. Cole, Cambridgeshire (GB); Michael J. Evans, Cambridge (GB); Julian A. Cluff, Cambridgeshire (GB)

(73) Assignee: TeraView Limited, Cambridge (GB)

( * ) Notice: Subject to any disclaimer, the term of this patent is extended or adjusted under 35 U.S.C. 154(b) by 475 days.

(21) Appl. No.: 10/526,560

(22) PCT Filed: Sep. 4, 2003

(86) PCT No.: PCT/GB03/03871

§ 371 (c)(1),
(2), (4) Date: Oct. 19, 2005

(87) PCT Pub. No.: WO2004/023611

PCT Pub. Date: Mar. 18, 2004

(65) Prior Publication Data

US 2006/0151722 A1     Jul. 13, 2006

(30) Foreign Application Priority Data

Sep. 4, 2002    (GB) ................................ 0220562.3

(51) Int. Cl.
*H01Q 5/00*    (2006.01)

(52) U.S. Cl. ............................. 343/700 MS; 250/493.1
(58) Field of Classification Search .............. 250/493.1; 343/700 MS
See application file for complete search history.

(56) References Cited

U.S. PATENT DOCUMENTS

| 5,894,125 A * | 4/1999 | Brener et al. ................ 250/330 |
| 2006/0152412 A1* | 7/2006 | Evans et al. ........... 343/700 MS |
| 2006/0231761 A1* | 10/2006 | Peytavit et al. ........... 250/338.1 |

FOREIGN PATENT DOCUMENTS

| EP | 0606776 | 7/1994 |
| JP | 2000-49403 | 2/2000 |

* cited by examiner

*Primary Examiner*—Nikita Wells
*Assistant Examiner*—Johnnie L Smith, II
(74) *Attorney, Agent, or Firm*—Dickstein Shapiro LLP

(57) ABSTRACT

An emitter for emitting radiation in a first range of frequencies comprising: a photoconductive material (11); and first and second contact elements (12, 13, 14) separated by a photoconducting gap provided by said photoconducting material (11), for applying a bias across said photoconducting gap, wherein at least one of said first and second contact elements (12, 13, 14) comprises a resistive element (14) for restricting current flow between said first and second contact elements in a second range of frequencies lower than the first range of frequencies.

26 Claims, 5 Drawing Sheets

COHERENT THZ EMITTER WITH DC POWER REDUCING RESISTOR

The present invention relates to emitters for the generation of radiation which can be used to image or determine compositional information from structures, particularly radiation in the frequency range colloquially referred to as Terahertz radiation. The range being that from 0.02 THz to 100 THz, particularly that in the range from 0.09 THz to 84 THz and especially that in the range from 0.1 THz to 20 THz.

Recently there has been much interest in using Terahertz (THz) radiation to look at a wide variety of samples using various methods. For example, THz radiation can be used for both imaging samples and obtaining spectra at each pixel in an image. THz radiation penetrates most dry, non-metallic and non-polar objects like plastic, paper, textiles, cardboard, semiconductors and non-polar organic substances. Therefore THz radiation can be used instead of x-rays to look inside boxes, cases etc. THz radiation also has medical uses.

One form of radiation is made up of short timescale broadband pulses. One of the most effective methods of generating broadband pulsed radiation utilises sub-picosecond optical/NIR laser pulses and a photoconductive emitter. To generate these pulses, a laser pulse of appropriate wavelength is directed onto the photoconductive emitter. When the emitter is biased and the light pulse used to illuminate the gap between the electrodes is sufficiently short (<1 picosecond) then the resulting current transient will radiate electromagnetic radiation in broadband away from the electrodes with frequencies extending into the Terahertz range.

This technique relies on laser excitation and suitably fabricated photoconductive devices. By definition, these photoconductive devices exhibit an increase in their electrical conductivity when exposed to light of a particular wavelength. This conductivity persists for a time corresponding to the "lifetime" of electrical charge carriers in the material. For example, for a GaAs photoconductive device the lifetime is typically of the order of 1 ns.

In its simplest form, a photoconductive emitter comprises two electrodes provided on a surface of a photoconductive material, such as a semiconductor material. Many semiconductor materials, such as GaAs and Si are photoconductive. To operate the emitter, a bias voltage is applied between the electrodes and the photoconductive material is exposed to a laser source of suitable wavelength. This significantly increases the conductivity of the semiconductor to the extent that a current flows through the material between the electrodes due to the presence of the bias electric field. Provided the bias field is maintained, the current will persist for a time corresponding to the lifetime of the photo-created charge carriers in the material.

The power emitted by a photoconductive device increases with the bias-voltage applied to the electrodes. Ultimately, the maximum voltage that can be applied is limited by the "dielectric breakdown" electric field value of the material concerned.

Device failure due to excessive power dissipation or excessive current density is most problematic in the narrower gap electrode designs, e.g. the interdigitated electrode arrangement which are typically run at higher repetition rates and hence higher powers. Large gap electrode designs which are run at high repetition rates similarly suffer from excessive power dissipation.

When the current densities flowing within the conductive contacts to the point of emission are sufficiently high, atomic motion induced by the current flow will occur in the conductor over a period of time, which can result in device failure (this phenomena is known as "electro-migration"). The onset of this phenomenon is typically considered to be in the region of 100,000 Acm$^2$. With current technologies, the thickness of the metal applied to the photoconductive devices is typically around 300 nm. This geometry with a typical current flow of the order of 1 mA results in current densities approaching the onset of electromigration. Therefore, premature device failure will occur for a given bias.

The thermal effects problem has been addressed by thermal management techniques such as heat sinking and air/water cooling.

The so-called "co-planar strip line emitter" refers to a form of emitter with an electrode having a strip line geometry on a photoconductive material. The high frequency performance of such emitters is acceptable, as low frequency radiation is suppressed by diverting the direction of current flow along the stripline conductors, which is orthogonal to the emitted THz polarisation.

Such emitters are typically run with a bias voltage of the order of 100V and at an average current of over 1 mA. Hence the power dissipated in the device is often over 100 mW in a volume of just a few cubic microns. The thermal effects problem in such devices has been considered by focussing the exciting laser along a line (rather than a point) at one electrode edge, thus distributing the emission along the line and reducing the current density. Although the line focus distributes the power dissipation over a larger area then the point focus, the total power dissipation in the device still remains high since the total current is similarly high. Therefore, the power dissipation problem is only partially mitigated by using such a line-focus technique, and heat sinking and water-cooling may still be required. Furthermore, the line-focus technique is more difficult to implement with a fibre-coupled THz device, and in particular with a THz probe system.

A photoconductive device, that is suitable for use in an emitter and which is able to minimise premature sample failure to prolong the life of the device, is therefore desirable.

It is particularly desirable to devise a photoconductive device, suitable for use in an emitter, which is able to minimise power dissipation.

It is an aim of the present invention to overcome or alleviate at least one of the problems of the prior art.

According to a first aspect, the present invention provides an emitter for emitting radiation in a first range of frequencies comprising:
  a photoconductive material; and
  first and second contact elements, separated by a photoconducting gap provided by said photoconductive material, for applying a bias across said photoconducting gap,
  at least one of said first and second contact elements comprising a resistive element for restricting current flow between said first and second contact elements in a second range of frequencies lower than the first range of frequencies.

The first and second contact elements may be provided by surface electrodes provided on an emission surface of the photoconductive material or provided on the surface of regions or layers of material which abut the photoconductive material. Alternatively, the contact elements may be provided by regions or layers of material which abut the photoconductive material. Any combination of the above may also be used.

At least one of the first and second contact elements may consist entirely of a resistive element however, preferably at least one of the contact elements comprises an antenna electrode provided in series with said resistive element. If such an antenna electrode is provided, it is provided adjacent said photoconducting gap and has a lower resistance than said resistive element.

Typically, said resistive element will have a resistance which is significantly higher than that of the antenna electrode, for example, preferably, at least five times the resistance of the antenna electrode.

The resistance of the resistive element should preferably be greater than the resistance of any feeding circuit provided for the emitter. Typically, the resistive element will have a resistance of at least 5 kΩ, preferably at least 10 kΩ, more preferably at least 30 kΩ, even more preferably at least 60 kΩ and most preferably at least 1 MΩ.

Optionally, a contact electrode may also be provided in series with said resistive element to allow external electrical connection to be made to said resistive element. If an antenna electrode is also provided, the antenna electrode, resistive element and contact electrode are provided respectively in series.

Preferably, both the first and second contact elements are the same. However, they do not necessarily need to be the same and may be provided by any combination of the above arrangement. For example: one contact element may solely comprise a resistive element and the other contact element may solely comprise a low resistance metallic surface electrode; one contact element comprising a resistive element and an antenna electrode and the other contact electrode comprising just a resistive element etc.

In the first aspect of the invention, it is preferable that the first range of frequencies falls within at least a part of the range from 0.02 THz to 100 THz, and more preferably within at least a part the range 3 THz to 100 THz.

In the above aspect, the power dissipation problem is addressed in that it has been found that the use of a resistive element with the electrodes advantageously serves to restrict the power dissipation in the device at low frequencies, without any significant impact on high frequency emission.

The resistive element is preferably integrated onto the photoconductive substrate, as this eliminates or at least reduces any parasitic capacitance between the emitting area (the antenna electrode) and the resistive element.

The first and second contact elements are preferably configured to form an antenna arrangement. For example, they may form a simple dipole antenna, a bow-tie antenna where at least a part of the two facing contact elements are formed to be generally triangular in shape and arranged in mirrored formation, the apexes may be blunted. Preferably, the edges of the contact elements provided adjacent the photoconducting gap are blunted or rounded. A so-called interdigitated electrode design may also be used.

Preferably, the facing edges of the contact elements, i.e. the edges of the contact elements which are adjacent to the photoconducting gap are recessed below the surface of the photoconducting material.

An emitter according to the invention may be utilised in apparatus for imaging or for determining compositional information of structures or in a system for generating and detecting terahertz radiation. Preferably such apparatus comprises a transformer for biasing the emitter with an AC voltage. It is also preferable that the apparatus further comprises a pulsed laser source. In the system for generating and detecting terahertz radiation, preferably the receiver comprises a bowtie antenna terahertz receiver.

The resistive element of the emitter comprises any suitable resistive material, which may include at least one of the following: Indium Tin Oxide, Indium Oxide, Tin Oxide, Indium Titanium Oxide, Titanium Oxide, Nickel-Chrome, doped Silicon Dioxide, Silicide, Poly-Silicon, Carbon, doped GaAs, lightly doped Silicon, nichrome or AlGaAs heterolayer.

The photoconductive material comprises any suitable material, which may include at least one of the following: Si, Ge, GaAs, As-implanted GaAs, InAs, ion-implanted Si, ion-implanted Ge, any other III-V group semiconductor, any other II-VI group semiconductor, any ion-implanted semiconductor and any low temperature grown epitaxial layer/semiconductor such as LT-GaAs, LT-InGaAs and LT-AlGaAs.

Most preferably the photoconductive device is fabricated from a short lifetime photoconductive material, such as LT-GaAs, As-implanted GaAs or radiation damaged silicon so that the electrical breakdown voltage of the device is maximised.

It is preferable that a dielectric film at least partially covers the emission surface of the emitter, and in particular it is preferred that the dielectric film covers the facing edges of the first and second contact elements.

The dielectric film may comprise at least one of the following: Silicon Nitride, Polyimide, Gallium Nitride, Acrylic or Silicon Dioxide.

According to a second aspect, the present invention provides a method of determining a resistive value for use as a series biasing resistance in a terahertz emitter, comprising:

determining a value indicative of a repetition frequency of an excitation laser;

determining a value indicative of a capacitance of the emitter; and calculating the resistive value by equating the value indicative of the repetition frequency with an RC-time constant of the terahertz emitter.

According to a third aspect, the present invention provides a method of determining a resistive value range for use as a series biasing resistance in a terahertz emitter, comprising:

determining a range of values indicative of a repetition frequency of an excitation laser;

determining a value indicative of a capacitance of the emitter; and calculating the resistive value range by equating the range of values indicative of the repetition frequency with an RC-time constant of the terahertz emitter.

According to a fourth aspect, the present invention provides a method for determining a resistive value, R, for use as a series biasing resistance in a terahertz emitter comprising a photoconductive substrate and an antenna electrode on the substrate surface, the method comprising:

determining the resistive value using the formula:

$$A=1/(RC)$$

where A is a repetition frequency of an excitation laser and C is the capacitance of the antenna electrode.

In the fourth aspect, it is preferable that C further comprises the capacitance of conductors between the resistive element and antenna, which feed the antenna.

This is because the resistive elements serve to isolate the antenna and its feed conductors from the outside world. Therefore capacitances of conductors outside of the resistive elements have little or no affect.

The second, third and fourth aspects of the invention provide for the determination of an optimum resistive value based on laser repetition frequency and device capacitance.

Although it is not essential to the first aspect of the invention to use a resistor having such a value, it is preferable to use a resistive element having a resistivity in accordance with that defined in the second to fourth aspects of the invention to enhance emission efficiency, power-handling and the lifetime of the emitter.

The present invention will now be described with reference to the following non-limiting embodiments in which.

Figure 1:
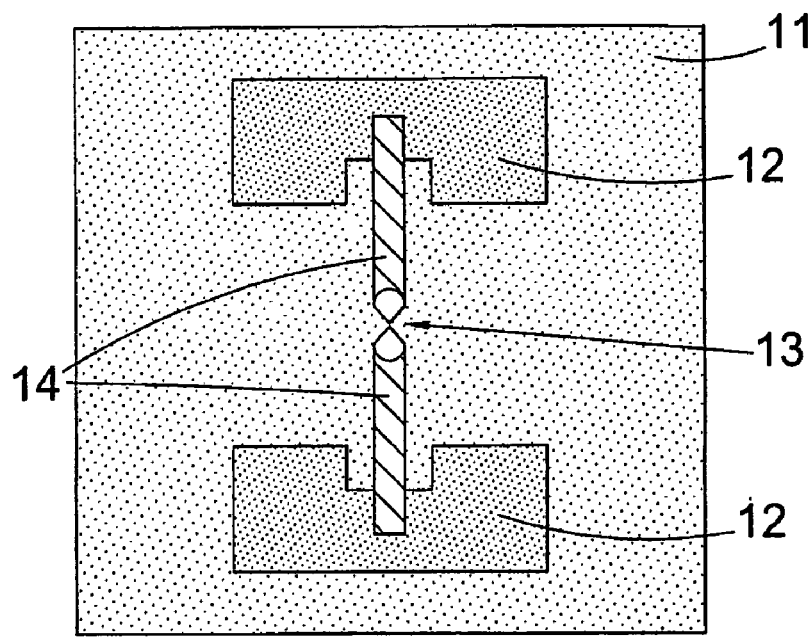
FIG. 1 shows a schematic diagram of a general form of an emitter according to an embodiment of the present invention.

With reference to FIG. 1, a general illustration of an emitter according to an embodiment of the present invention is shown. The illustrated emitter comprises a GaAs photoconductive material as a substrate 11 with a contact element assembly (12, 13, 14) provided on a surface thereof.

The photoconductive substrate 11 may comprise any suitable photoconductive material, including Si, Ge, GaAs, As-implanted GaAs, InAs, ion-implanted Si, ion-implanted Ge, any other III-V group semiconductor, any other II-VI group semiconductor and any ion-implanted epitaxial layer/semiconductor such as LT-GaAs.

Each contact element has three main components, being the first and second contact electrodes 12, resistive element 14 and the antenna electrodes 13. The contact electrodes 12 are located opposite one another on the surface of the photoconductive material in mirrored relation. The antenna electrodes 13 are provided between the first and second contact electrodes 12. In this embodiment, the antenna electrodes 13 are constructed from two regions of conductive material separated by a small gap, which together form a dipole antenna.

It is to be appreciated that the contact electrodes 12 and the antenna electrodes 13 can be formed from any highly conductive material such as gold, copper, silver or alloys thereof, Ti—Pd—Au, Ti—Pt—Au, Ti—Ni—Ag, Al, Mo silicides and poly-doped silicon.

In this embodiment of the invention the resistive element 14 of the electrode assembly is in the form of two high resistivity strips, provided in series between the contact electrodes 12 and the antenna electrodes 13. Each resistive strip extends between a contact electrode and the central antenna electrode. Each resistive strip may be considered to be associated respectively with one of the first and second contact electrodes 12, so that each resistive strip/contact electrode combination can be considered to form a conductive terminal.

Preferably the resistive element 14 is integrated on the photoconductive substrate 11 by integrating the resistive element onto the emitter device die. In this regard, "integrated" is intended to mean that the resistive element is lithographically formed on the same semiconductor chip as the antenna-electrodes and photoconductive material.

The resistive element 14 may be created by evaporating strips of thin film Indium Tin Oxide (ITO) onto the substrate area, as electrical feed lines. The exact nature of the resistive element, particularly in terms of composition, is not critical. For example, other suitable materials for the resistive element include Indium Oxide, Tin Oxide, Indium Titanium Oxide, Titanium Oxide, Nickel-Chrome, doped Silicon Dioxide, Silicide, Poly-Silicon, Carbon, doped GaAs, lightly doped Silicon, nichrome or AlGaAs heterolayer. These layers may be fabricated using standard photolithographic procedures.

The exact position and structure of the resistive element on the substrate is also not critical, provided the resistive element is located so as to at least partially restrict current flow between the electrodes at low emission frequencies. For example, the resistive element need not be comprised of two resistive strips: a single resistive element in the gap between the contact terminals would be within the scope of the present invention as it would exhibit similar benefits to having two strips. Similarly, the resistive element, particularly where comprised of one or more resistive strips, need only extend partially between the contact electrode and the antenna electrode, or equivalently, between the contact electrode and the photoconductive gap. When the resistive element only partially extends between the contact electrode and antenna electrode or the contact electrode and photoconducting gap, a lower resistance element is used to complete the circuit.

The present invention may also be implemented without an antenna electrode. That is, an emitter according to the present invention may comprise two contact electrodes with a photoconductive gap there between and a resistive element associated with one or both of the contact electrodes. In such a configuration the photoconductive gap would provide the emission.

Further, the exact resistance value of the resistive element 14 is not critical, provided that it is sufficiently large so that when in series between the contact electrodes and the antenna electrode or photoconductive gap, the resistive element prevents or at least minimises excessive current flow at low emission frequencies (e.g. <1 THz) while at high frequencies, such as THz frequencies, the resistive element 14 has little effect on the performance of the emitter. In general, the higher the resistance, the less low frequency current that flows and accordingly the less power dissipated in the device. Therefore, by incorporating the large resistive element on the photoconductive substrate, the high frequency performance of the THz emitter is increased and also the power dissipation of the device is reduced.

In operation, the contact electrodes 12 are connected to an external bias circuit (not shown) and the antenna electrodes 13 are excited by one or more lasers.

Terahertz emission occurs during the very fast rise-time of the current flow in the photoconductive device (i.e. the first picosecond or so), however power dissipation persists for as long as the current flows, typically for up to one nanosecond. This is the case even for nominally "short-lifetime" photoconductive materials such as LT-GaAs, As-implanted GaAs or radiation-damaged silicon, since the presence of the large biasing electric field prevents efficient recombination of the charge carriers.

With a resistive element in place, at lower emission frequencies, the current flow between the contact electrodes 12 is largely stopped by the resistive element 14. Hence, decreased power dissipation in the device is achieved and device failure due to current-induced thermal damage no longer occurs, or at least rarely occurs. Hence, integrated resistor emitter devices may be biased to higher bias voltages than emitter devices without such a resistor, as the resistive element advantageously increases the THz power available from a comparable emitter.

With such integrated resistor emitter devices, since higher bias voltages may be applied, the performance of the integrated resistor emitter is more likely to be ultimately limited by electrical breakdown in the device. Therefore, to further maximise the performance of the emitter, steps should be taken to suppress electrical breakdown.

For example, a photoconductive material with a strong avalanche breakdown resistance will aid in maximising the current through the device during THz generation. Suitable materials include LT-GaAs, ion-implanted GaAs, As-implanted GaAs, radiation damaged silicon and any LT-grown semiconductor material.

Figure 2:
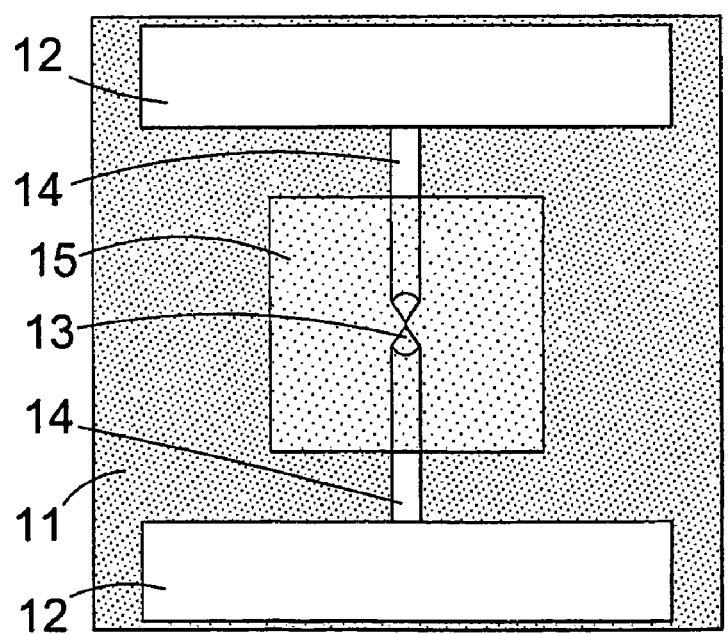
FIG. 2 shows a schematic diagram of a general form of an emitter overlaid with a dielectric film according to an embodiment of the present invention.

Another feature that may be incorporated into the emitter to suppress electrical breakdown is a dielectric film over the surface of the device. FIG. 2 illustrates the emitter of FIG. 1, comprising a substrate 11 with a contact element assembly (12, 13, 14) provided on a surface thereof. A dielectric film 15 is provided at least partially over the surface of the emitter. In the illustrated example of FIG. 2, the dielectric wholly covers the antenna electrodes 13.

Figure 3:
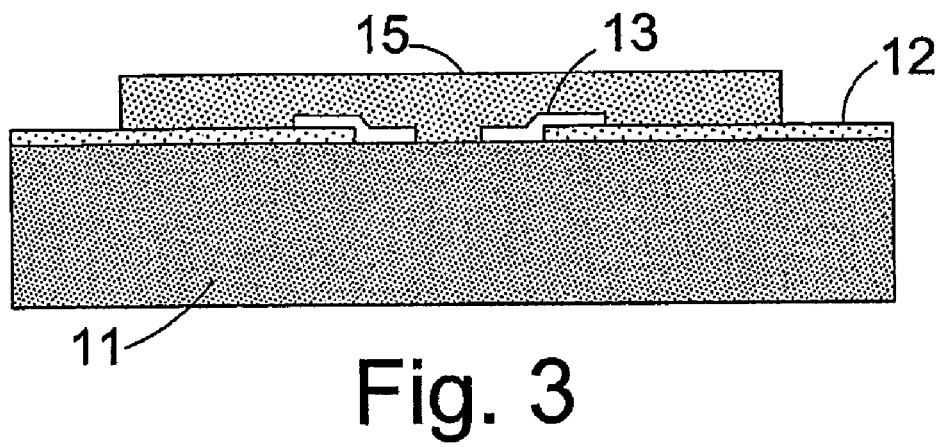
FIG. 3 shows a side view of the emitter of FIG. 2 overlaid with the dielectric film.

With reference to FIG. 3, which shows a side view of the FIG. 2 emitter with the dielectric film 15 over the antenna electrodes 13, it is evident that the dielectric film 15 at least substantially covers all surfaces of the antenna electrodes 13 that would be otherwise be exposed beyond the surface of the substrate. By providing such a film, particularly over the electrode areas of the device, electrical breakdown is suppressed. This is because the dielectric coating fills the gap between the two antenna electrodes, and since the breakdown field of the dielectric is higher than that of the bare semiconductor surface or surrounding air, its presence increases the overall breakdown resistance of the device.

Further the presence of the dielectric suppresses electromigration across the surface of the device. The dielectric film is capable of achieving this result as it suppresses surface conduction and arcing across the device surface. That is, the film is a solid which acts as a barrier to electromigration. The metal atoms cannot move into the gap between the electrodes as this space is already taken up by the dielectric material.

Suitable dielectric coatings include silicon nitride, polyimide, Gallium Nitride, acrylic and silicon dioxide. This dielectric film may also serve as an anti-reflective coating.

Electrical breakdown and electromigration may be further reduced by recessing the antenna electrode region below the surface of the semiconductor wafer. Preferably the electrodes are recessed to just below the surface. By recessing the electrodes, a physical boundary is provided which prevents, or at least reduces, electromigration and the effects thereof. It is believed that by recessing the terminals a current flow at least substantially perpendicular to the sides of the recessed pits is achieved which serves to reduce current density, power dissipation and thermal effects.

An emitter constructed according to the invention is preferably utilised in a system for generating and detecting high frequency radiation such as THz radiation. With such systems, high voltage electronics are generally required to provide the bias-signal source. Such electronics are not necessary, however if a step-up transformer is provided between the bias-signal source and the emitter device. An example of a suitable excitation circuit is illustrated in FIG. 9.

Figure 9:
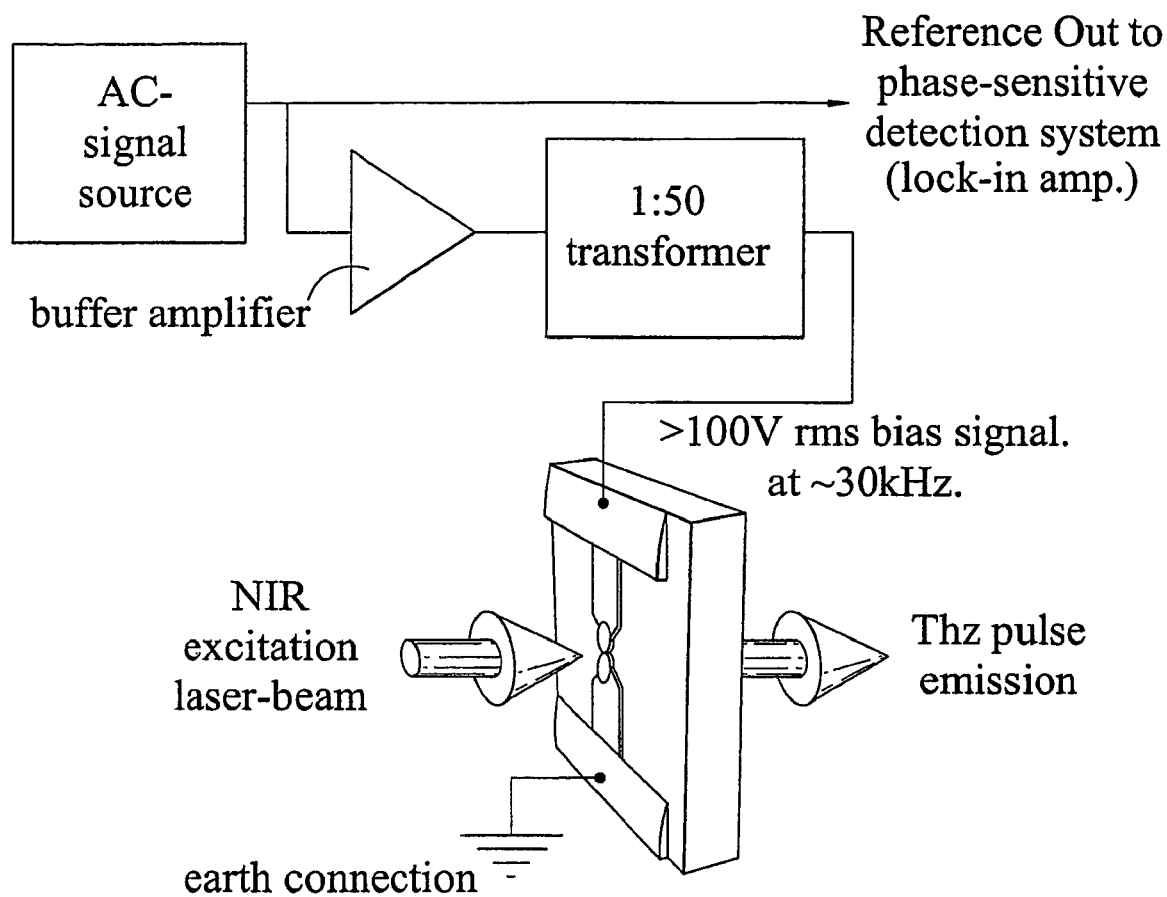
FIG. 9 illustrates an excitation circuit for providing an excitation pulse signal to an emitter according to an embodiment of the present invention.

In the example of FIG. 9, the signal from an AC signal source 91 is input to a 1:50 transformer 93 via a power amplifier 92. The output from the AC signal source 91 may also be provided as a phase reference signal for an emission detector (not shown).

The output of the step-up transformer 91 is then input to the electrodes of the photoconductive emitter 94. The step-up transformer 93 is adapted to provide the emitter with a large AC bias voltage, as opposed to a DC bias. The AC bias flips back and forth between the anode and the cathode of the emitter 94, which serves to minimise the stresses that occur with DC currents and aids in prolonging the life of the emitter.

FIG. 9 also illustrates the emitter 94 receiving a pulsed excitation signal 95, such as from a pulsed NIR laser, in addition to the large AC bias voltage from the transformer, in order to produce a pulsed emission 96, such as pulsed THz emission.

Where a 50:1 step-up transformer is used, the input voltage may be in the range of 1 to 5V RMS. With such an input, an output in the range of 50 to 250 V RMS could be expected. Where it is intended to produce THz radiation, preferably the AC bias voltage generated by the transformer 93 is greater than 100V RMS at approximately 30 kHz. The maximum voltage that can be applied to the emitter essentially depends upon the breakdown resistance of the emitter.

As compared with a typical 500V, 10 Watt DC power supply, which is large and expensive, the arrangement of FIG. 9 is able to produce large voltages via a smaller and cheaper configuration. More specifically, a smaller configuration is achievable as 1:50 transformers are typically only a few cubic-cm in volume, and can be driven by a 20 W power amplifier, which is a generally cheap component. The power required is quite small because the current in the emitter is low.

To illustrate the effectiveness of an emitter constructed according to the present invention, consider a THz emitter fabricated with an approximate total resistance between the contact electrodes and the antenna electrodes of 60 kΩ and a rounded-dipole antenna design with electrodes 70 micron long from tip to tip.

Figure 4:
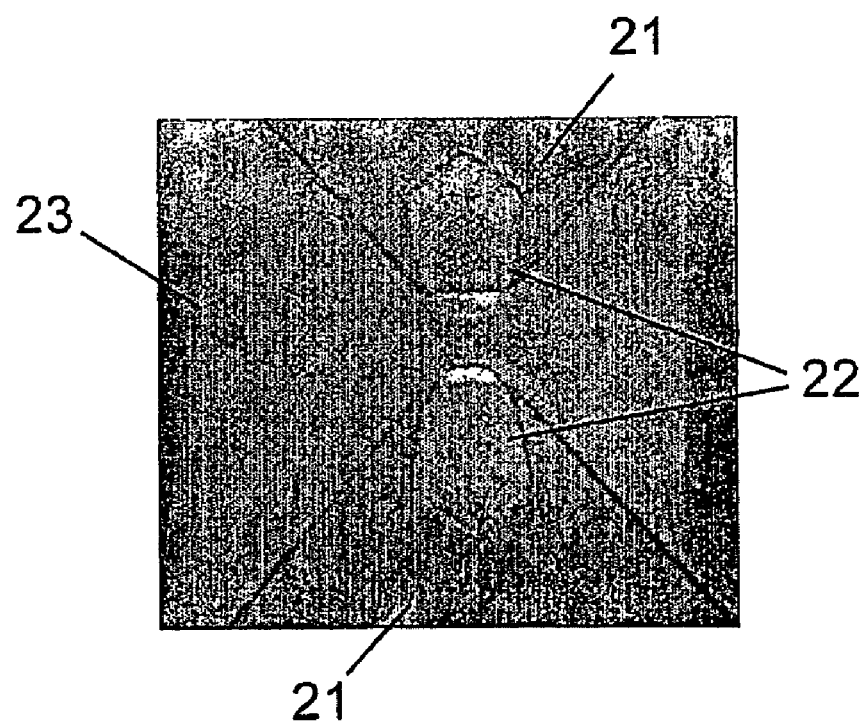
FIG. 4 shows an enlarged photograph of the antenna region of a dipole emitter constructed according to an embodiment of the present invention.

An enlarged photograph of such an emitter is shown in FIG. 4. The resistive elements 21 on the surface of the photoconductive substrate were made by evaporating a thin film of Indium Titanium Oxide onto the lithographically masked device with a GaAs substrate 23. The antenna electrodes 22 and contact electrodes (not shown) were made by evaporating titanium-gold layers onto the surface of the resistive elements 21.

Figure 5:
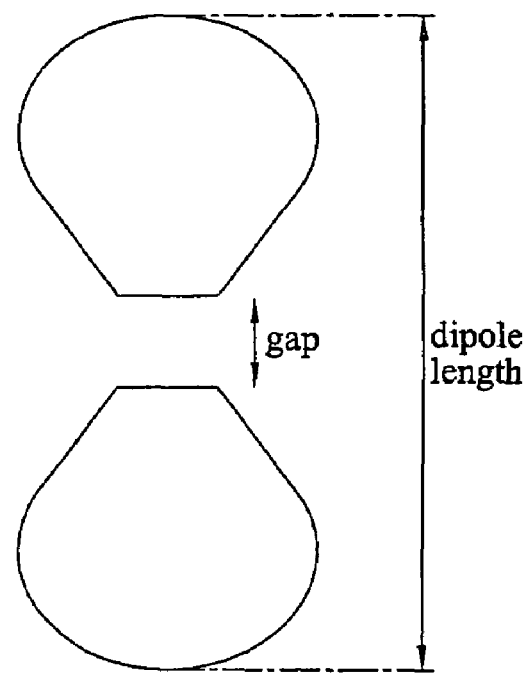
FIG. 5 shows a plan view of a typical rounded dipole antenna that may be utilised in an emitter according to an embodiment of the present invention.

The antenna electrodes 22 form a dipole antenna consisting of two dipoles in a mirrored relationship. The shapes of the two dipoles 22 in the photograph of FIG. 4 shows more of a pentagonal shape rather than a rounded shape. The gap between the two antenna dipoles 22 is four microns. FIG. 5 illustrates schematically the typical shape of a "rounded dipole" antenna, with the two rounded dipoles in a mirrored relationship and separated by a gap.

To illustrate its operation, this emitter of FIG. 4 was AC biased at a sinusoidal frequency of 33 kHz using a 50:1 step-up transformer. Optical excitation was provided by 100 fs pulses from a Vitesse™ coherent Ti:sapphire laser. The THz detection was provided by a standard bowtie shaped THz photoconductive receiver. For comparison similar measurements were performed using a conventional bowtie-shaped THz emitter without a series resistive element.

Figure 7:
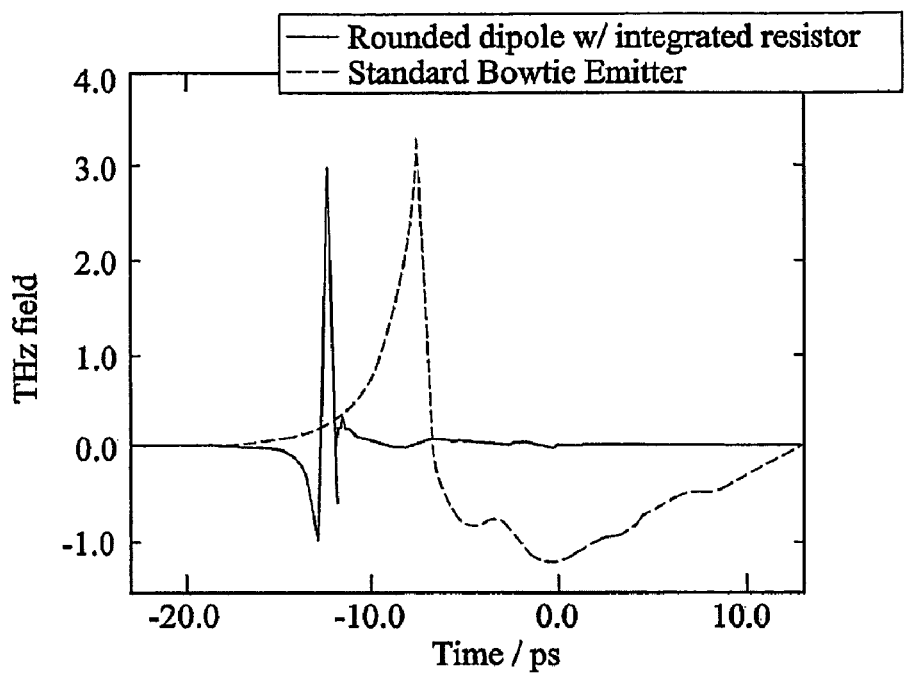
FIG. 7 shows a THz pulse generated by the rounded dipole shaped emitter of FIG. 4 compared with that from a standard bow-tie shaped emitter.

FIG. 7 illustrates the THz pulse shape obtained from the Integrated Resistor THz emitter of FIG. 4 as compared to the THz pulse from a standard bowtie shaped emitter without the resistive element. A pulse was obtained from both emitters, but the pulse obtained from the Integrated Resistor emitter is "sharper". That is, there is virtually no low frequency resonance after the main THz pulse for the integrated resistor emitter. The standard bow-tie design emitter, on the other hand exhibits a substantial low frequency resonance. Importantly, this sharper pulse was obtained with little loss of peak amplitude of the pulse.

Figure 8:
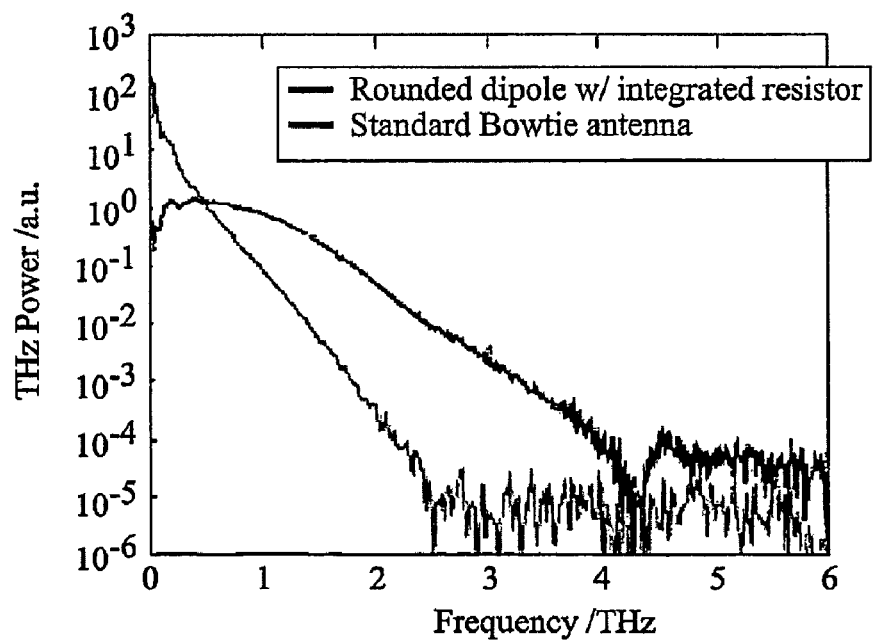
FIG. 8 shows the frequency domain power spectra for the integrated resistor emitter and the standard bowtie emitter obtained using the time domain data of FIG. 7.

FIG. 8 illustrates the data of FIG. 7 in the Frequency Domain, which is obtained by applying a Fourier Transform to the Time Domain data. From the frequency domain power spectra it is clear that the high frequency performance of the Integrated Resistor design is substantially superior to the bowtie design. For example, at a frequency of 3 THz, the new design generates well over 100 times more power than the standard bowtie design. Although the total emitted power over all frequencies is greater for the standard bowtie design, this is due to extremely strong emissions at very low frequencies (<100 GHz), which is generally undesirable in Terahertz radiation generation.

FIG. 8 also illustrates that the combination of a standard bowtie design with an integrated resistor is a particularly beneficial combination, since the combination of both devices produces a non-resonant frequency response that extends over the range from 10 GHz to over 4 Hz. Further, at 1 THz, the power lever is virtually flat, which is close to ideal.

According to another aspect of the invention there are preferred resistive values for the resistive element of the emitter depending upon the antenna device geometry. Although these resistive values are not essential for implementing the integrated resistor emitter, device performance may be optimised via this aspect of the invention, which will now be described.

By viewing the THz antenna structure as a capacitor (C), which is charged through the series feed resistor (R), the charging time for the capacitor is characterised by the RC-time constant for the system. A suitable RC value is approximately equal to the time between optical excitation pulses. If the RC-time constant is much longer than the inter-pulse time, then the bias-field across the electrodes is reduced and hence less THz power is emitted. On the other hand, if the RC time constant is much less than the charge carrier lifetime in the semiconductor, then the surplus photocurrent is increased, which in turn increases the device power consumption and leads to earlier device failure. Therefore, there are preferred RC values about the time value between excitation pulses.

Figure 6:
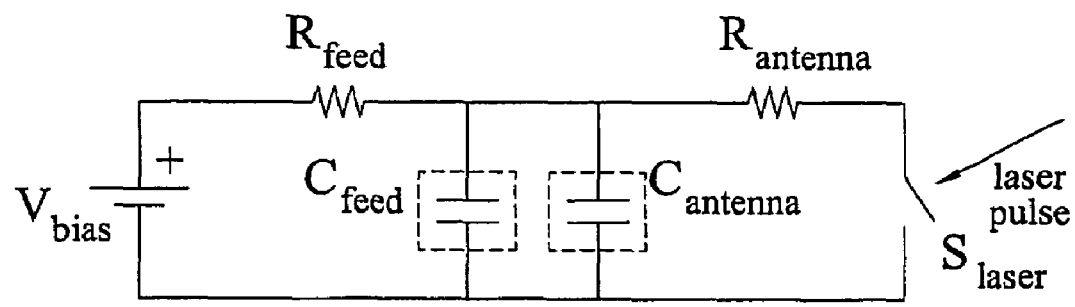
FIG. 6 shows a schematic circuit diagram approximation of a THz photoconductive emitter according to an embodiment of the present invention.

With reference to FIG. 6, a circuit diagram approximation is shown of an emitter according to an embodiment of the present invention. $R_{antenna}$ is the characteristic impedance of the antenna and represents the resistance of the photoconductive region of the emitter after optical excitation. That is, from a physical standpoint it simulates the load imposed on the current in the antenna by the surrounding space. For most antenna geometries, such as bowtie and rounded dipole, $R_{antenna}$ lies in the range of 20 to 200 ohms. $R_{feed}$ represents the series feed-resistance.

The capacitance of the antenna is $C_{antenna}$ and the capacitance of the conductors feeding the antenna is $C_{feed}$. For example, a one meter length of typical coaxial cable might have a capacitance of 100 pF. As illustrated in FIG. 6, $R_{antenna}$ and $R_{feed}$ are to be considered in series with bias voltage $V_{bias}$. $C_{antenna}$ and $C_{feed}$, on the other hand are to be considered in parallel with $V_{bias}$. The energising laser pulse is illustrated as a switch $S_{laser}$, which opens and closes the series circuit between the resistances and $V_{bias}$ as appropriate.

Between optical pulses energy is stored in the combined capacitance of the antenna and feed conductors ($C_{total}=C_{antenna}+C_{feed}$). Optical excitation results in the capacitors discharging through the photoconductive element of the device, so dissipating the stored energy in the photoconductor $R_{antenna}$. Excessive power dissipation in $R_{antenna}$ will lead to device failure, and hence should be minimised such as by including an optimised $R_{feed}$.

The capacitance of the emitting structure can be minimised by making the size of the antenna electrodes as small as possible. Not only does this reduce the overall capacitance, but it advantageously serves to improve the high frequency performance of the device while reducing the overall power dissipated. Preferably the gap size is matched to laser focus size, and a focus size of 2-4 microns is optimal for a laser pulse energy of 0.25 nJ. Note that for different laser pulse energies, the optimal focus size should be scaled to maintain a constant pulse area energy density. Therefore, for a laser pulse of four times the energy, the optimal focus size would increase by two (i.e. $\sqrt{4}$). The antennal electrode size determines the high frequency roll-off of the antenna and is tailored according to the response desired for a particular application, however a typical preferred range would be 10 to 100 micron. Note that this is the end-to-end length or dipole length, as illustrated in FIG. 5 (i.e. each electrode is approximately half this length).

Considering a GaAs based THz emitter and an 80 MHz rep-rate laser, the time between optical excitation pulses is 12 nanoseconds. Based upon this, the optimum RC value is 12 ns, with some benefit to device performance to be expected with RC values one order of magnitude either side of this (i.e. 1.2 ns to 120 ns).

Using Finite Difference Time-Domain (FDTD) calculations, a 600 micron length bowtie antenna on a GaAs substrate should have a capacitance roughly independent of the size of the gap between electrodes and be of approximately 50 fF. Hence, for a 600 micron standard bowtie device, with $C_{feed}$ minimised, $C_{total}$ is approximately equal to $C_{antenna}$ and, calculated from the RC time constant, a suitable series resistance is 240 kΩ.

For a 70 micron rounded dipole antenna design, the capacitance is reduced to 6.2 fF, but the self-capacitance of the resistive element itself should also be taken into account when calculating a suitable resistance value, which would bring the value of $C_{antenna}$ up to 14 fF. Thus for a 70 micron rounded-dipole device, with $C_{feed}$ minimised, $C_{total}$ is approximately equal to $C_{antenna}$ and, calculated from the RC time constant target, a suitable series resistance is 860 kΩ.

Variations and additions are possible within the general inventive concept as will be apparent to those skilled in the art. It will be appreciated that the broad inventive concept of the present invention may be applied to any conventional type of pulsed emission system and that the exact embodiment shown is intended to be merely illustrative and not limitative. For example, the present invention may be readily applied to a number of different photoconductive emitter geometries such as the so-called co-planar stripline.

Further, the emitter of the present invention may be used in various forms, such as in a combined THz generation and detection system. When used in this form, the THz detector preferably includes a bowtie-antenna THz receiver used in combination with an integrated resistor THz emitter, as the combination is almost completely broadband.

The invention claimed is:

1. An emitter for emitting radiation in a first range of frequencies comprising:
   a photoconductive material; and
   first and second contact elements separated by a photoconducting gap provided by said photoconducting material, for applying a bias across said photoconducting gap,
   wherein at least one of said first and second contact elements comprises a resistive element for restricting current flow between said first and second contact elements in a second range of frequencies lower than the first range of frequencies.

2. An emitter according to claim 1, wherein the first range of frequencies falls within at least a part of the frequency range from 0.02 THz to 100 THz.

3. An emitter according to claim 1, wherein said at least one contact element further comprises an antenna electrode provided in series with said resistive element, said antenna electrode being provided adjacent said photoconducting gap and having a lower resistance than said resistive element.

4. An emitter according to claim 1, wherein said at least one electrode further comprises a contact electrode provided in series with said resistive element, to allow an external electrical connection to be made to said resistive element.

5. An emitter according to claim 1, wherein the resistive element is integrated onto the emitter.

6. An emitter according to claim 1, wherein the resistive element comprises at least one of the following:
   Indium Tin Oxide, Indium Oxide, Tin Oxide, Indium Titanium Oxide, Titanium Oxide, Nickel-Chrome, doped Silicon Dioxide, Silicide, Poly-Silicon, Carbon, doped GaAs, lightly doped Silicon, nichrome or AlGaAs heterolayer.

7. An emitter according to claim 1, wherein the photoconductive material comprises at least one of the following:
   Si, Ge, GaAs, LT-GaAs, As-implanted GaAs, InAs, ion-implanted Si, ion-implanted Ge, LT-InAs, LT-InGaAs, LT-AlGaAs, a III-V group semiconductor, a II-VI group semiconductor, an ion-implanted semiconductor and a low temperature grown semiconductor.

8. An emitter according to claim 1, further comprising a dielectric film at least partially covering an emission surface of the emitter.

9. An emitter according to claim 3, wherein a dielectric film at least partially covers the antenna electrode.

10. An emitter according to claim 1, wherein a dielectric film at least partially covers the photoconductive gap.

11. An emitter according to claim 8, wherein the dielectric film comprises at least one of the following:
    Silicon Nitride, Polyimide, Gallium Nitride, Acrylic or Silicon Dioxide.

12. An emitter according to claim 1, wherein the edges of the contact elements which are adjacent the photoconducting gap are recessed below the surface of the photoconductive material.

13. An emitter according to claim 1, wherein the edges of the first and second contact elements provided adjacent the photoconducting gap are rounded.

14. An emitter according to claim 1, wherein said resistive element has a resistance R, where $$R > \frac{1}{AC}$$

where A is the repetition frequency of an excitation laser and C is the capacitance of the contact elements.

15. An emitter according to claim 1, wherein said resistive element has a resistance of at least 5 k$\Omega$.

16. A method of determining a resistive value for use as a biasing resistance in a terahertz emitter, comprising:
    determining a value indicative of a repetition frequency of an excitation laser;
    determining a value indicative of a capacitance of the emitter; and
    calculating the resistive value by equating the value indicative of the repetition frequency with an RC-time constant of the terahertz emitter.

17. A method for determining a resistive value, R, for use as a series biasing resistance in a terahertz emitter comprising a photoconductive substrate and an antenna electrode on the substrate surface, the method comprising:
    determining the resistive value using the formula:

$A=1/(RC)$ where A is a repetition frequency of an excitation laser and C is the capacitance of the antenna electrode.

18. The method of claim 17, wherein C further comprises the capacitance of conductors between the resistive element and an antenna, which feed the antenna.

19. An apparatus for imaging comprising an emitter as claimed claim 1.

20. An apparatus for determining compositional information of structures comprising an emitter as claimed in claim 1.

21. The apparatus of claim 19, further comprising a transformer for biasing the emitter with an AC voltage.

22. The apparatus of claim 19, further comprising a pulsed laser source.

23. A system for generating and detecting terahertz radiation including an emitter as claimed in claim 1, and a detector which comprises a bowtie antenna terahertz receiver.

24. A system for generating THz radiation, comprising:
    an emitter comprising a photoconductive material and first and second contact elements separated by a photoconducting gap provided by said photoconducting material for applying a bias across said photoconducting gap,
    a bias signal source for said emitter configured to output and AC signal; and
    a step-up transformer located between said bias signal source and said emitter.

25. A system according to claim 24, wherein said bias signal source is configured to output a signal having a voltage in the range from 1V to 5V.

26. A system according to claim 24, wherein said transformer has a ratio of 1:50.

* * * * *